United States Patent
Nukui

(10) Patent No.: US 7,372,936 B2
(45) Date of Patent: May 13, 2008

(54) RADIATION COMPUTED TOMOGRAPHY APPARATUS AND TOMOGRAPHIC IMAGE DATA GENERATING METHOD

(75) Inventor: Masatake Nukui, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 15 days.

(21) Appl. No.: 10/940,904

(22) Filed: Sep. 14, 2004

(65) Prior Publication Data

US 2005/0063518 A1    Mar. 24, 2005

(30) Foreign Application Priority Data

Sep. 19, 2003    (JP)    ............................. 2003-327412

(51) Int. Cl.
G21K 1/10 (2006.01)
G21K 1/04 (2006.01)
G01D 18/00 (2006.01)

(52) U.S. Cl. ........................... 378/7; 378/150; 378/207

(58) Field of Classification Search .............. 378/4–20, 378/98.12, 207, 901, 86–87, 147–154
See application file for complete search history.

(56) References Cited

U.S. PATENT DOCUMENTS

| 4,081,681 | A | * | 3/1978 | Froggatt | ........................ | 378/7 |
| 4,233,507 | A |  | 11/1980 | Volz |  |  |
| 4,266,135 | A | * | 5/1981 | Kuwik et al. | ................. | 378/16 |
| 4,296,329 | A |  | 10/1981 | Mirabella |  |  |
| 4,352,020 | A |  | 9/1982 | Horiba et al. |  |  |
| 4,375,695 | A | * | 3/1983 | Harding et al. | ................ | 378/6 |
| 4,656,650 | A | * | 4/1987 | Kikuchi et al. | ................ | 378/7 |
| 4,787,098 | A | * | 11/1988 | Silver | .......................... | 378/18 |
| 4,897,788 | A |  | 1/1990 | King |  |  |
| 5,214,578 | A |  | 5/1993 | Cornuejols et al. |  |  |
| 5,442,674 | A |  | 8/1995 | Picard et al. |  |  |

(Continued)

FOREIGN PATENT DOCUMENTS

EP    0652537    3/1994

(Continued)

OTHER PUBLICATIONS

European Patent Office Search Report; 154282/10235; 04255642.3-2305-; GE Medical Systems Global Technology Company LLC; 4 pgs.

(Continued)

*Primary Examiner*—Edward J. Glick
*Assistant Examiner*—Anastasia S. Midkiff
(74) *Attorney, Agent, or Firm*—Armstrong Teasdale LLP

(57) ABSTRACT

A radiation computed tomography apparatus that includes a radiation detector having a plurality of radiation detector elements arranged in a two-dimensional manner for detecting radiation passing through a subject, and a reconstructing device for arithmetically reconstructing tomographic image data for a tomographic image of the subject based on projection data for the subject from each of the plurality of radiation detector elements, the projection data obtained from values detected by the plurality of radiation detector elements, wherein the reconstructing device corrects the projection data for each of the radiation detector elements using a corrective value that is correlated with a path length of the radiation through the subject calculated from the projection data, and generates the tomographic image data based on the corrected projection data.

18 Claims, 8 Drawing Sheets

U.S. PATENT DOCUMENTS

| | | | |
|---|---|---|---|
| 5,461,651 A * | 10/1995 | Tam | 378/4 |
| 5,774,519 A | 6/1998 | Lindstrom et al. | |
| 5,821,541 A | 10/1998 | Tumer | |
| 6,275,559 B1 | 8/2001 | Ramani et al. | |
| 6,325,539 B1 | 12/2001 | Bromberg et al. | |
| 6,639,964 B2 | 10/2003 | Schneider et al. | |
| 6,901,130 B2 * | 5/2005 | Bruder et al. | 378/4 |
| 2002/0106052 A1 * | 8/2002 | Menhardt | 378/4 |
| 2003/0128801 A1 * | 7/2003 | Eisenberg et al. | 378/19 |

FOREIGN PATENT DOCUMENTS

| | | |
|---|---|---|
| JP | 07-184886 | 7/1995 |
| SE | 526371 C2 * | 8/2005 |

OTHER PUBLICATIONS

Peter M. Joseph; The Effects of Scatter in X-Ray Computer Tomography; Med. Phys. 9(4), Jul./Aug. 1982, pp. 464-472; XP-002274892.

B. Ohnesorge et al; Efficient Object Scatter Correction Algorithm for Third and Fourth Generation CT Scanners; Eur. Radiol. 9, 563-569 (1999) XP-002274890.

M. Endo et al.; Development and Performance Evaluation of the First Model of 4D Ct-Scanner; BNSDOCID: XP10663877A 1; 0-7803-7636-6/03/$ 17.00 (2003 IEEE), pp. 1824-1828.

* cited by examiner

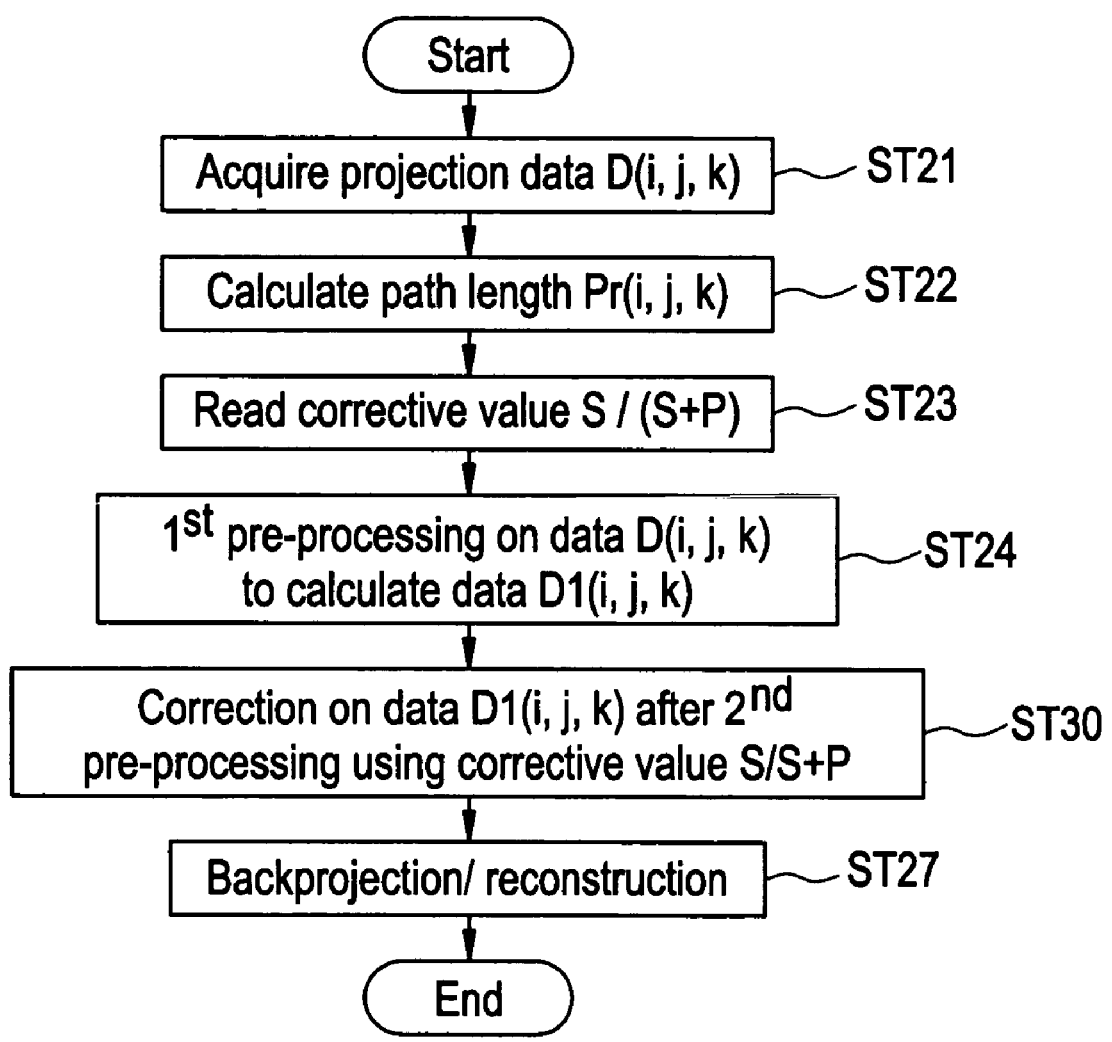

RADIATION COMPUTED TOMOGRAPHY APPARATUS AND TOMOGRAPHIC IMAGE DATA GENERATING METHOD

CROSS REFERENCE TO RELATED APPLICATIONS

This application claims the benefit of Japanese Application No. 2003-327412 filed Sep. 19, 2003.

BACKGROUND OF THE INVENTION

The present invention relates to a radiation computed tomography apparatus capable of acquiring volume data, such as a VCT (volume CT (computed tomography)) apparatus or a multi-row CT apparatus, and a tomographic image data generating method in the radiation computed tomography apparatus.

Particularly, the present invention relates to a radiation computed tomography apparatus and tomographic image data generating method for reducing the influence by scatter rays through correction.

Known X-ray CT apparatuses include, for example, one that acquires projection data for a subject by an X-ray detector having a plurality of X-ray detector elements arranged in a two-dimensional manner. The plurality of X-ray detector elements are positioned to have their width in a direction along a predefined axis with respect to the subject. Since X-ray detector element rows are formed over a certain width in the axis direction, the X-ray detector having X-ray detector elements arranged in a two-dimensional manner is generally referred to as a multi-row detector.

In the multi-row detector, a direction along the axis is sometimes referred to as a column direction, and a direction orthogonal to the column direction as a channel direction, for example.

In the X-ray CT apparatus comprising the multi-row detector, projection data of a cross section of the subject is acquired by emitting an X-ray fan beam, which has an extent in both the column and channel directions, from a predefined focal spot at a plurality of positions around the axis to the multi-row detector.

A tomographic image of the subject is produced by a reconstruction calculation based on the projection data.

Such an X-ray detector having a two-dimensional extent increases the probability that the detecting surface is struck also by X-rays other than those directly impinging upon a detecting surface from a focal spot, i.e., for example, by scatter X-rays (scatter rays) caused by X-rays having their direction of travel deflected due to collision with an object, such as bone, in the subject.

Especially, as an increase of the number of rows in the multi-row detector enlarges the width of the X-ray fan beam in the column direction, the fan beam is directed onto a wider area in the subject, resulting in generation of more scatter rays. As a result, the probability that scatter rays impinge upon the X-ray detector elements is increased accordingly.

The scatter rays contain projection information on the subject that the X-ray detector elements receiving the scatter rays should not detect. Therefore, the scatter rays cause generation of artifacts, and image quality of the tomographic image may be degraded.

To reduce such an influence by scatter rays, various techniques have been proposed. For example, Patent Document 1 discloses a CT apparatus for calculating a deconvolution function for reconstruction of a tomographic image from an arithmetically obtained elastic (coherent) scatter function of scatter rays, and reconstructing a tomographic image using the deconvolution function that corrects the influence by coherent scatter rays.

[Patent Document 1] Japanese Patent Application Laid Open No. H7-184886.

In the CT apparatus described in Patent Document 1, however, the width of opening (aperture) for an X-ray beam in the column direction is not particularly taken into account. Thus, it cannot fully deal with the multi-row detector.

As explained above, conventional techniques do not fully correct and reduce the influence by scatter rays, which increases with increasing number of X-ray detector rows, so that there is a need to further improve image quality of tomographic images.

SUMMARY OF THE INVENTION

It is therefore an object of the present invention to provide a radiation computed tomography apparatus capable of reducing artifacts in a tomographic image by more effectively correcting the influence by scatter rays.

It is another object of the present invention to provide a tomographic image data generating method capable of reducing artifacts in a tomographic image by more effectively correcting the influence by scatter rays in a radiation computed tomography apparatus.

A radiation computed tomography apparatus in accordance with the present invention comprises a radiation detector having a plurality of radiation detector elements arranged in a two-dimensional manner for detecting radiation passing through a subject, and reconstructing means for arithmetically reconstructing tomographic image data for a tomographic image of said subject based on projection data for said subject from each of said plurality of radiation detector elements, said projection data obtained from values detected by said plurality of radiation detector elements, wherein said reconstructing means corrects said projection data for each of said radiation detector elements using a corrective value that is correlated with a path length of said radiation through said subject calculated from said projection data, and generates said tomographic image data based on said corrected projection data.

A tomographic image data generating method in accordance with the present invention, implemented in a radiation computed tomography apparatus comprising a radiation detector having a plurality of radiation detector elements arranged in a two-dimensional manner for detecting radiation passing through a subject, and reconstructing means for arithmetically reconstructing tomographic image data for a tomographic image of said subject based on projection data for said subject from each of said plurality of radiation detector elements, said projection data obtained from values detected by said plurality of radiation detector elements, comprises a step of utilizing said reconstructing means to correct said projection data using a corrective value that is correlated with a path length of radiation through a subject calculated from said projection data, and a step of generating said tomographic image data based on said projection data corrected by said reconstructing means.

In the present invention, a plurality of radiation detector elements for detecting radiation are arranged to have a two-dimensional extent. The radiation detector elements detect radiation passing through the subject, whereby projection data of the subject by the radiation are generated for each of the radiation detector elements.

The reconstructing means calculates a path length of the radiation through the subject based on the projection data obtained for each of the radiation detector elements. The reconstructing means corrects the projection data using a corrective value that is correlated with the path length. The reconstructing means then generates tomographic image data for the subject based on the corrected projection data.

According to the present invention, the influence by scatter rays can be more effectively corrected to reduce artifacts in a tomographic image.

The present invention can be applied to an X-ray CT apparatus or VCT apparatus.

Further objects and advantages of the present invention will be apparent from the following description of the preferred embodiments of the invention as illustrated in the accompanying drawings.

BRIEF DESCRIPTION OF THE DWINGS

FIG. 9 is a chart showing a procedure for generating tomographic image data using the corrective value in accordance with a variation of the present invention.

DETAILED DESCRIPTION OF THE INVENTION

Embodiments of the present invention will now be described with reference to the accompanying drawings. It should be noted that radiation in the present invention includes X-rays. The following description will be made exemplifying an X-ray CT apparatus employing X-rays as the radiation.

Figure 1:
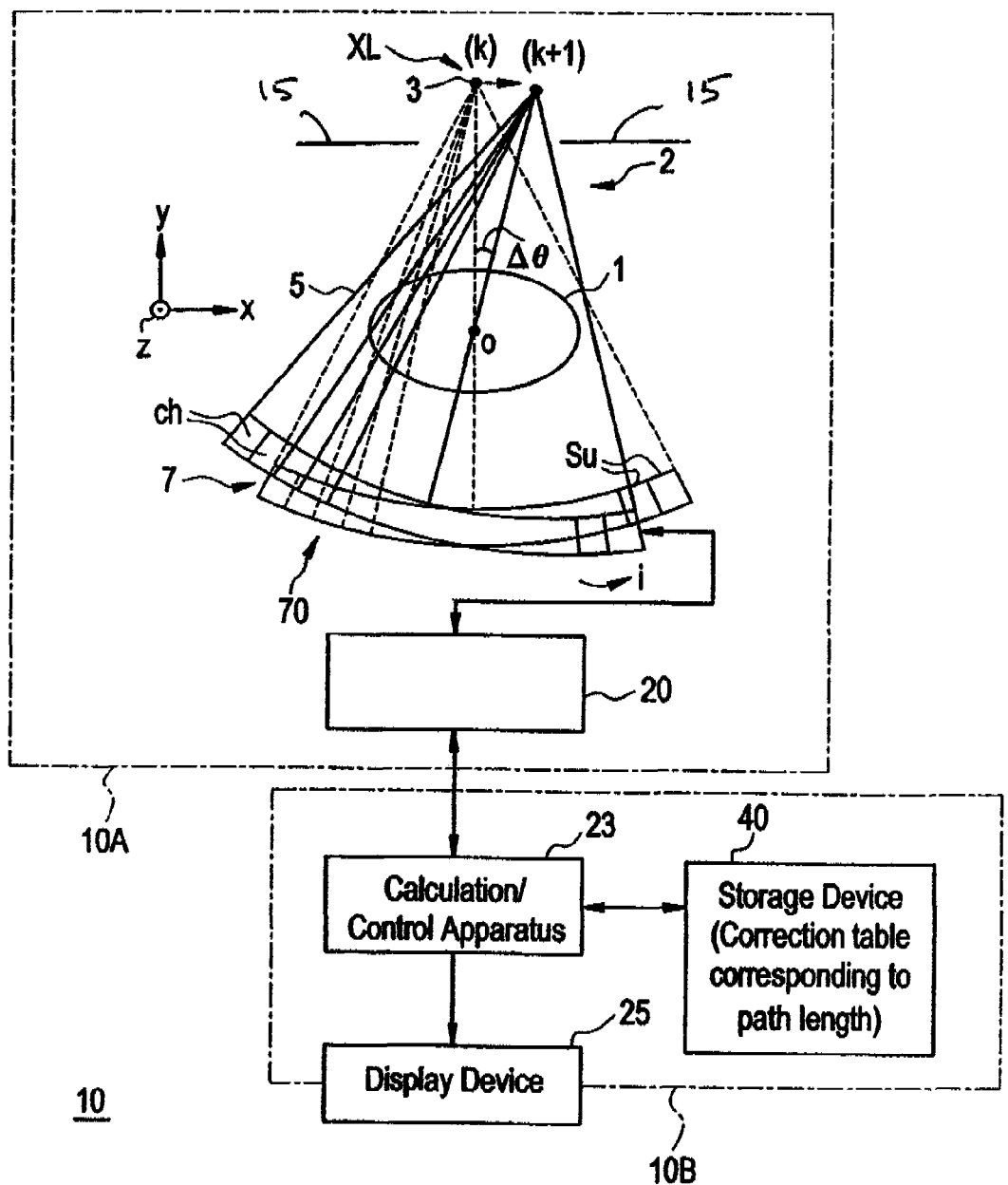
FIG. 1 is a diagram showing the general configuration of an X-ray CT apparatus in accordance with an embodiment of the present invention.

FIG. 1 is a diagram showing a general configuration of an X-ray CT apparatus in accordance with an embodiment of the present invention. The X-ray CT apparatus 10 shown in FIG. 1 comprises an X-ray CT apparatus main body 10A and a console 10B. One embodiment of the radiation computed tomography apparatus in accordance with the present invention is the X-ray CT apparatus 10 shown in FIG. 1.

The X-ray CT apparatus main body 10A comprises a rotating section 2 and a data acquisition system (DAS) 20, as shown in FIG. 1.

The rotating section 2 comprises an X-ray source XL for emitting X-rays, and an X-ray detector 70 for detecting the X-rays emitted by the X-ray source XL.

The X-ray source XL emits a fan-shaped X-ray beam 5 from an X-ray focal spot 3. The fan-shaped X-ray beam 5 is sometimes referred to as a fan beam.

The intensity of the X-ray beam 5 is detected by an X-ray detector 70.

A subject 1 is positioned between the X-ray source XL and X-ray detector 70. The X-ray source XL and X-ray detector 70 of the X-ray CT apparatus 10 in accordance with the present embodiment are rotated around a predefined axis O by the rotating section 2 as shown in FIG. 1 while maintaining their positional relationship relative to each other. For example, the body axis direction of the subject 1 from head to toe is made to coincide with the direction of the axis O. Moreover, the direction of the axis O coincides with a z-axis direction in FIG. 1.

An embodiment of the axis of rotation in accordance with the present invention corresponds to the axis O.

The X-ray detector 70 has a plurality of detector channels ch arranged in a two-dimensional matrix (array). An embodiment of the radiation detector elements in accordance with the present invention corresponds to the detector channels ch.

Figure 7:
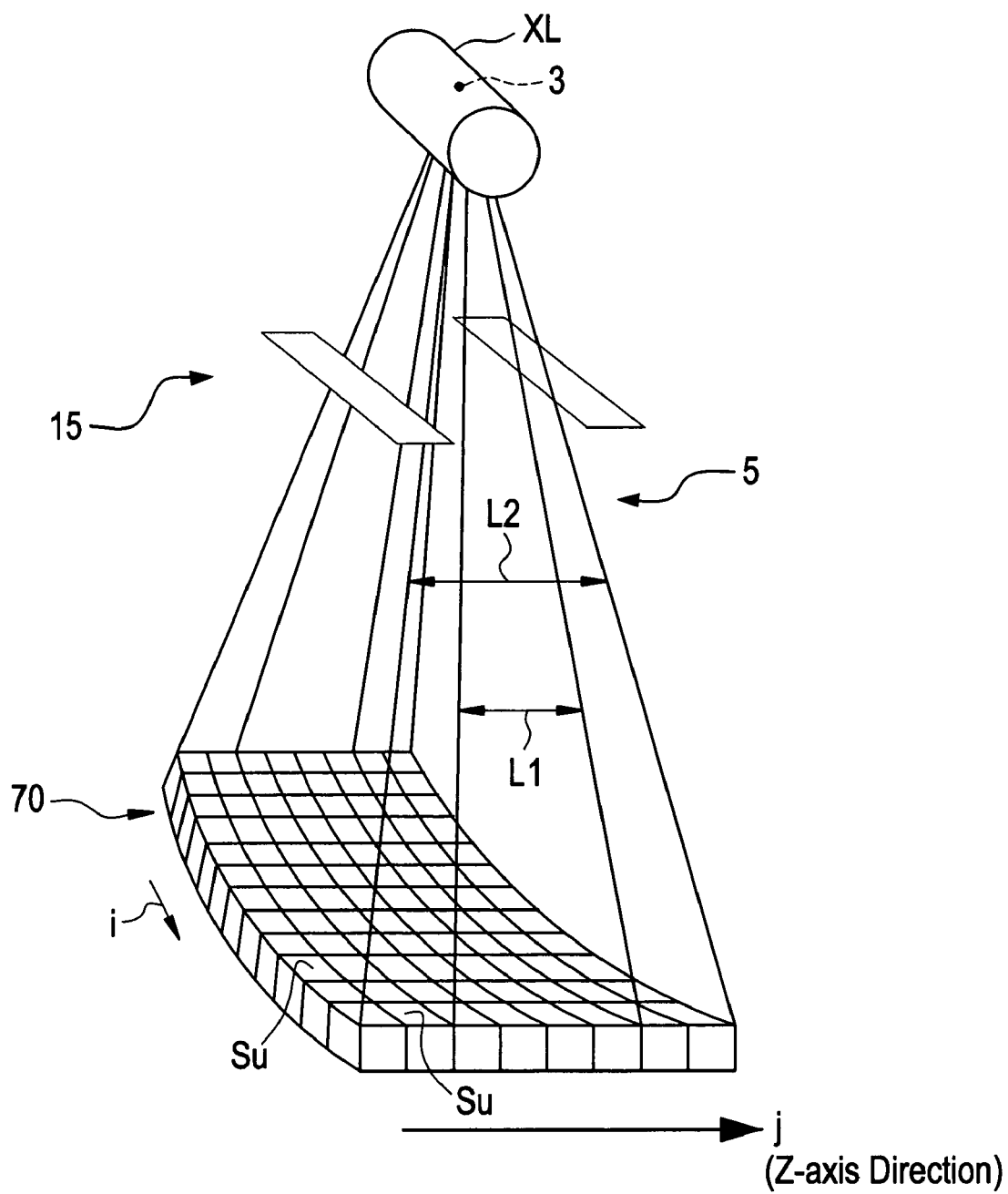
FIG. 7 is a perspective view representing the relationship among the X-ray source, X-ray focal spot, X-ray beam and X-ray detector.

The detector channels ch arranged in a two-dimensional manner are designated by a column index i along the row direction and a row index j along the column direction (shown in FIG. 7).

The row direction is sometimes referred to as the channel direction here. The detector channels ch lined up in a row in the channel direction are together referred to as a detector channel row.

In the column direction, a plurality of detector channel rows 7 are disposed juxtaposed to one another in parallel.

In FIG. 1, the X-ray detector 70 is illustrated in a cross section containing the channel direction.

An embodiment of the first arrangement direction in the present invention corresponds to the row direction (channel direction), and an embodiment of the second arrangement direction corresponds to the column direction.

The number of column indices, or channel indices, i is of the order of 1000, for example, and the number of row indices j is of the order of 16, for example.

Moreover, each detector channel ch is made by, for example, a combination of a scintillator and a photodiode.

As shown in FIG. 1, the column direction in the X-ray detector 70 is defined as the z-axis direction. A plane orthogonal to the z-axis is defined as an x-y plane.

The X-ray beam 5 is a fan beam having an extent in both the x-y and x-z planes.

The radiation detecting surface (referred to simply as the detecting surface hereinbelow) Su of each detector channel ch can individually and independently detect X-ray intensity of the X-ray beam 5, and data corresponding to the number of the detector channels ch arranged in a two-dimensional manner can be obtained.

The detecting surface Su of each detector channel ch is directed toward the X-ray focal spot 3 in the channel direction as shown in FIG. 1, and is directed toward the X-ray focal spot 3 and also toward the other directions in the column direction along the z-axis direction.

In other words, the plurality of detector channels ch are arranged in the channel direction to form a curve along the direction of rotation around the axis O, and flatly arranged in the column direction orthogonal to the channel direction.

Collection of X-ray intensity data is achieved by a scan in which the intensity of the X-ray beam 5 passing through subject 1 is detected by the detector channels ch in a varying direction of emission of the X-ray beam 5 toward the subject 1 while rotating the X-ray source XL and X-ray detector 70 around the axis O by the rotating section 2. Data in a plurality of directions in one rotation around the axis O are thus obtained. The direction of data collection is referred to as a view. In FIG. 1, a reference symbol k represents a view index. The number of views per rotation is of the order of 1000, for example. In this case, the spacing $\Delta\theta$ between the views shown in FIG. 1 is of the order of 360°/1000.

The DAS 20 collects a plurality of sets of the data acquired by the X-ray detector 70. The DAS 20 converts analog data of X-ray intensity detected by the X-ray detector 70 into digital data, and sends them to the console 10B.

The digital data sent to the console 10B represents projection data of a cross-sectional plane through which the X-ray beam 5 passes in the subject 1.

As shown in FIG. 1, the console 10B comprises a calculation/control apparatus 23, a storage device 40, and a display device 25.

An embodiment of the reconstructing means in the present invention corresponds to the calculation/control apparatus 23.

The calculation/control apparatus 23 is implemented by hardware, such as a CPU (central processing unit), and software for driving the hardware, for example.

The storage device 40 employed is a semiconductor RAM (random access memory) and a hard disk drive, for example.

The storage device 40 stores a correction table corresponding to the length over which the X-ray beam 5 passes through the subject 1, i.e., the path length.

Corrective values constituting the correction table will be described later.

The calculation/control apparatus 23 receives the projection data collected by the DAS 20. The calculation/control apparatus 23 performs a reconstruction calculation, such as backprojection, based on the received projection data to generate image data.

In the reconstruction, the calculation/control apparatus 23 accesses the storage device 40, and corrects the projection data based on a corrective value read out from the correction table. The calculation/control apparatus 23 then generates image data based on the corrected projection data.

The image data generated by the calculation/control apparatus 23 represents an image of a cross section through which the X-ray beam 5 passes in the subject 1, i.e., image data for a tomographic image (tomographic image data).

The tomographic image data can also be stored in the storage device 40.

Moreover, the calculation/control apparatus 23 controls the X-ray CT apparatus 10 for tomographic image production to execute operations including rotation of the X-ray source XL and X-ray detector 70 by the rotating section 2 and acquisition of projection data via the DAS 20.

Furthermore, the calculation/control apparatus 23 conducts control for displaying the produced tomographic image or a tomographic image based on tomographic image data stored in the storage device 40 on a display device 25 such as a CRT (cathode-ray tube) and a liquid crystal display panel. The display device 25 also displays an operation image for operating the X-ray CT apparatus 10.

The calculation/control apparatus 23 is connected with an input device, such as a keyboard (not shown). Via the input device, instructions from a human operator operating the X-ray CT apparatus 10 are input to the calculation/control apparatus 23.

In the present embodiment, the correction table stored in the storage device 40 is for the purpose of correcting the influence by scatter X-rays (scatter rays) in a scan on the subject 1 using the X-ray CT apparatus 10. The scatter rays are caused by X-rays having their direction of travel deflected due to collision with an object that has extremely different X-ray permeability, such as bone, in the subject. Therefore, it can be considered that some scatter rays will always be generated in a scan on the subject 1.

Moreover, as an increase of the number of detector channel rows 7 in the X-ray detector 70 enlarges the beam width of the X-ray beam 5 in the column direction, more scatter rays tend to be generated and the influence by scatter rays becomes larger.

The scatter rays are generated by the X-ray beam 5 passing through the subject 1. Thus, the magnitude or extent of the scatter rays depends primarily upon the subject 1, and the difference due to the system configuration of the X-ray CT apparatus 10, for example, the difference in the positional relationship between the X-ray source XL and X-ray detector 70, is considered to be small. Therefore, the corrective values in the correction table are appropriately defined by correlating them with the path lengths, and the values thus defined may be applied to X-ray CT apparatuses having any system configuration.

However, to determine the value correlated with the path length, and to precisely deal with change of an X-ray CT apparatus 10 over time, calibration for normalizing the corrective value to the path length is preferably conducted.

Thus, a procedure for the calibration will be described in detail hereinbelow with reference to FIG. 2.

Figure 2:
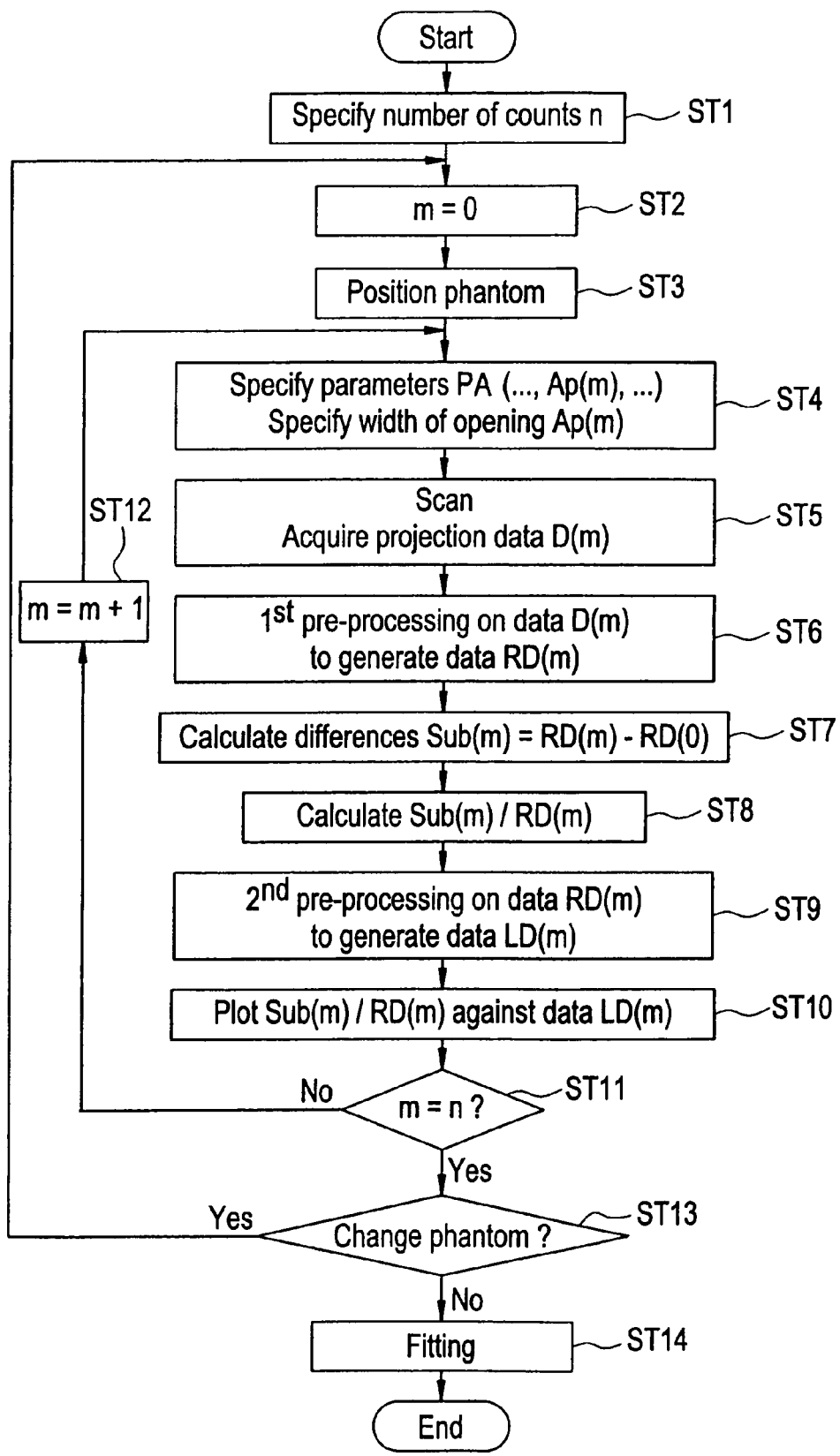
FIG. 2 is a flow chart showing an exemplary calibration procedure for calculating a path length of an X-ray beam through a subject and a corrective value corresponding to the path length.

FIG. 2 is a flow chart showing an exemplary procedure of the calibration for determining a path length of the X-ray beam 5 through the subject 1, and a corrective value corresponding to the path length.

In the calibration, a number of counts n is first specified (Step ST1).

The number of counts n represents the number of times of execution of the calibration with a varying parameter value affecting the corrective value. An example of the parameter employed is the width of opening (aperture) of the X-ray beam 5 defined by a collimator 15, illustrated in Fig 7, provided between the X-ray source XL and subject 1. The width of opening defines the shape of the X-ray beam 5 and determines the width of the X-ray beam 5 in the column direction.

Since the number of counts n significantly affects accuracy of the correction on a tomographic image by the corrective value, it is preferably selected taking various factors into account.

The value of the number of counts n is a natural number.

After specifying the number of counts n, a value m of a counter for counting the number of counts is set to an initial value m=0 (Step ST2).

Next, a phantom substituting for the subject 1 is positioned between the X-ray source XL and X-ray detector 70 for conducting a scan (Step ST3).

To determine a corrective value corresponding to a path length, X-ray detected data at different path lengths are needed. Therefore, an elliptical phantom PM having an elliptical cross section in the x-y plane is used as the phantom, as exemplarily shown in FIGS. 3(a) and (b).

Figure 3A:
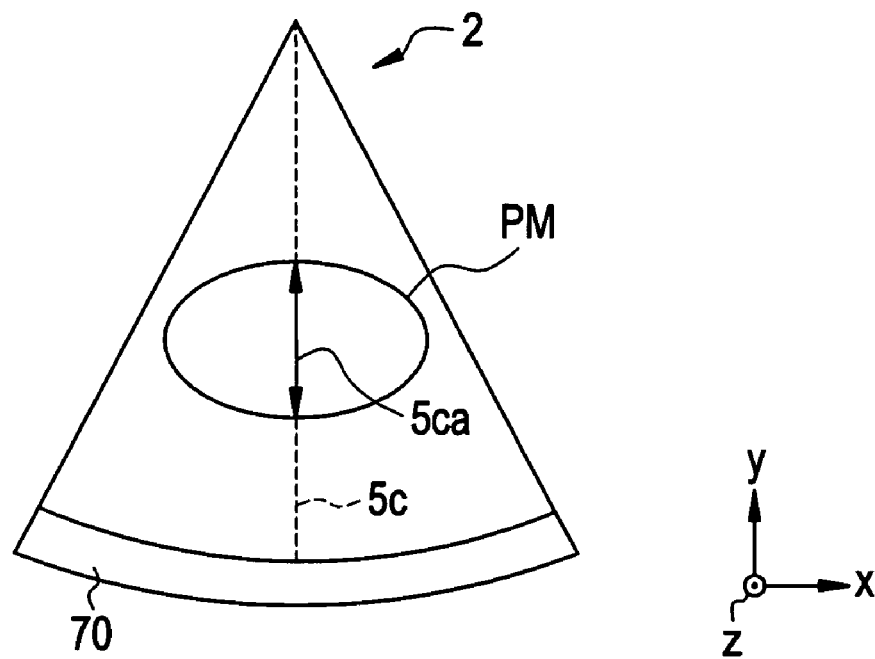
FIG. 3 is a diagram showing the positional relationship between a phantom and a rotating section, in which (a) shows the positional relationship in a certain view, and (b) shows the positional relationship in another view.
Figure 3B:
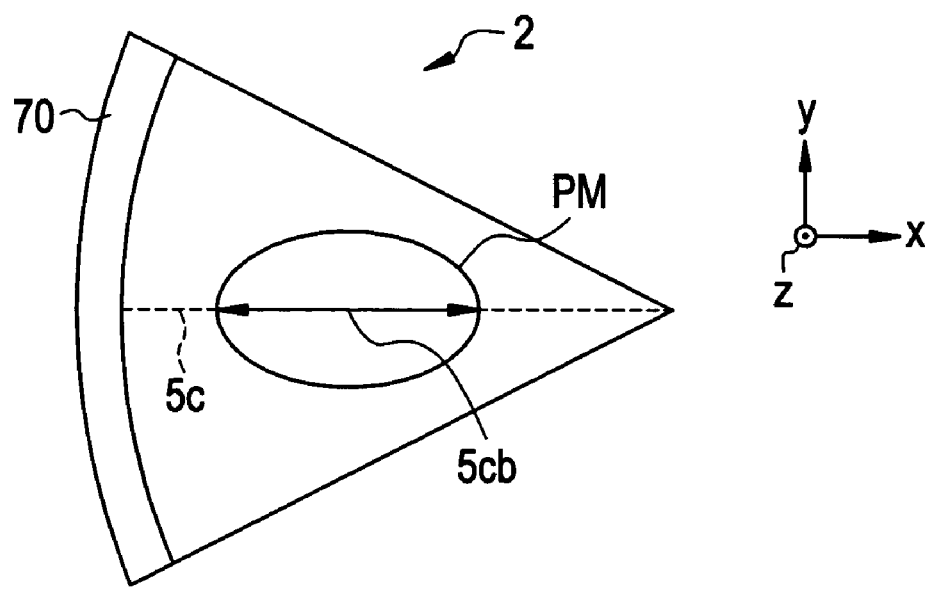

FIG. 3(a) shows a positional relationship between the rotating section 2 and elliptical phantom PM in a certain view, and FIG. 3(b) shows their positional relationship in another view. As shown in FIGS. 3(a) and (b), the use of the elliptical phantom PM allows a path length 5ca in a certain view and a path length 5cb in another view, for example, to be differentiated even for the same X-ray beam 5c whose intensity is detected by a detector channel ch in the center of the X-ray detector 70.

Instead of the elliptical phantom PM, a plurality of circular cylindrical phantoms having different diameters may be used one by one.

Prior to a scan, several kinds of parameters PA for the X-ray CT apparatus 10 are specified (Step ST4).

Preferred parameters PA are those affecting the corrective value, and include, for example, the aforementioned width of opening of the X-ray beam 5, the region in a tomographic image to be reconstructed, and the voltage to be applied to the X-ray source XL. Differentiation of the path length of the X-ray beam 5 using the elliptical phantom PM may be considered to be included in variation in the parameters PA.

For simplification, only the width of opening AP(m) is specified to vary with the value m of the counter here.

The value for the width of opening AP(m) employed is, for example, the width of a slit in the collimator 15 disposed adjacent to the X-ray source XL on the side of the X-ray detector 70 for defining the extent of the X-ray beam 5. The width may be appropriately changed within a range of, for example, 10-60 mm.

The width of opening AP(0) as a baseline for the first-time calibration in which m=0 is, for example, AP(0)=10 mm.

Since the width of opening AP(0) is relatively small, i.e., of the order of 10 mm, the region in the X-ray detector 70 onto which X-ray beam 5 impinges is small, and the influence by scatter rays is relatively small. It is preferable to thus set the width of opening AP(0) as a baseline to a relatively small width of opening.

After setting the width of opening AP(m), the X-ray CT apparatus 10 is used to scan the elliptical phantom PM, and projection data is acquired (Step ST5).

A general description on a scan by the X-ray CT apparatus 10 was set out earlier and is omitted here. The projection data is obtained for the number of views used in the scan for every detector channel ch.

The projection data obtained at Step ST5 is defined as projection data D(m).

The calculation/control apparatus 23 applies first pre-processing to the projection data D(m) obtained at Step ST5, including offset correction and reference correction (Step ST6).

Since offset correction, reference correction and other such processing are conducted before back-projecting the projection data D(m) to generate image data, they are called pre-processing.

The offset correction is a process of correcting an offset value incorporated in the detected data mainly due to the drift of an A-D (analog-to-digital) converter contained in the DAS 20.

The reference correction is a process for correcting variation in intensity of X-rays emitted from the X-ray source XL. X-rays emitted from the X-ray source XL do not always have the same intensity, and the intensity of the emitted X-rays may vary under some conditions. In such a case, the ratio between projection data D(m) from a detector channel generally referred to as a reference channel, i.e., a detector channel ch upon which X-rays not passing through any object always impinge even if an object such as the subject 1 or phantom is present, and projection data D(m) from other detector channels ch can be used to correct the variation in intensity of the emitted X-rays.

The projection data D(m) after the first pre-processing is designated as data RD(m).

Figure 4A:
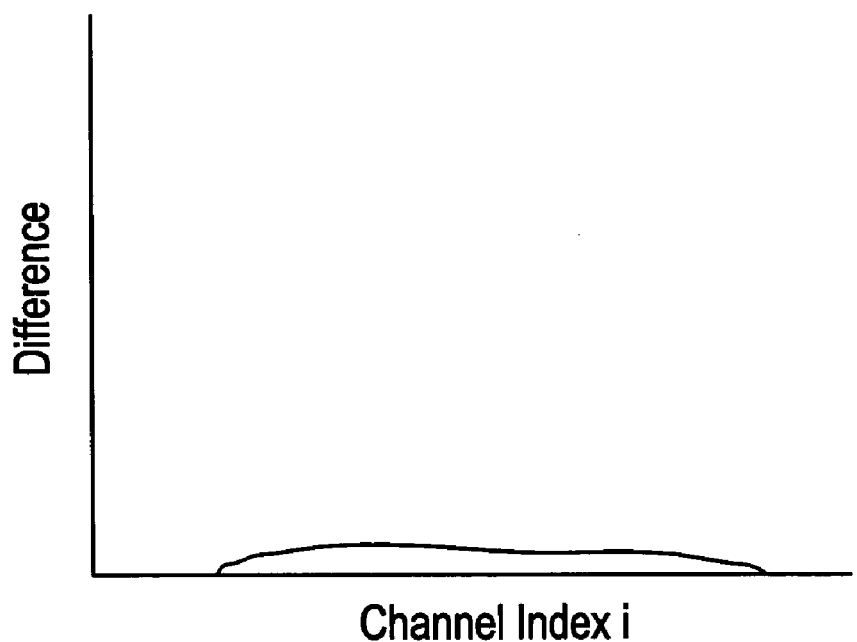
FIG. 4 is a graph representing the magnitude of the difference of data in one detector channel row, in which (a) shows exemplary values in a certain view, and (b) shows exemplary values in another view.

The calculation/control apparatus 23 uses the data RD(m) to calculate a difference $Sub(m)=RD(m)-RD(0)$ for each detector channel ch, as shown in FIGS. 4(a) and (b) (Step ST7).

The graphs shown in FIGS. 4(a) and (b) show the magnitude of the difference Sub(m) in one detector channel row 7, with the horizontal axis representing the channel index i, and the vertical axis representing the magnitude of the difference Sub(m), in which (a) shows exemplary values in a certain view, and (b) shows exemplary values in another view. As shown in FIG. 3, the area of projection of the elliptical phantom PM onto the X-ray detector 70 is different from view to view, and therefore, a range of the channel indices i having a non-null value of the difference Sub(m) is different from view to view, as shown in FIGS. 4(a) and (b).

As described above, a number of the differences Sub(m), which number is the same as the number of detector channels ch, are calculated for each view. The values of the differences Sub(m) thus obtained are stored in the storage device 40.

When m=0, Sub(0)=0; and since the condition m=0 is considered to be a baseline in which the influence by scatter rays is almost absent, Sub(0)=0 is used as is and the data RD(0) is stored in the storage device 40.

Since the value of the data RD(0) is considered to contain almost no influence by scatter rays, the difference $Sub(m)=RD(m)-RD(0)$ can be considered to represent the magnitude of scatter rays.

Next, the calculation/control apparatus 23 calculates the ratio Sub(m)/RD(m) (Step ST8).

The calculation of the ratio Sub(m)/RD(m) provides the proportion of the intensity S of scatter rays in the sum of the intensity P of X-rays that directly reach each detector channel ch from the X-ray source XL and the intensity S of scatter rays, i.e., in the value detected by each detector channel ch.

The ratio Sub(m)/RD(m) for each detector channel ch in each view is also stored in the storage device 40.

Moreover, the calculation/control apparatus 23 applies second pre-processing on the data RD(m) calculated at Step ST6 (Step ST9).

The second pre-processing includes calculation of $-\log(RD(m))$, for example.

The data RD(m) after the second pre-processing is designated as data LD(m).

The data LD(m) enables the magnitude of projection data for each detector channel ch to be quantitatively evaluated.

Since each detector channel ch is struck by the X-ray beam 5 at a different path length, the value of data LD(m) can be considered to have correlation with the path length. Therefore, the value of the data LD(m) may be regarded as the path length, and the path length to each detector channel ch can be obtained for each view, as shown in FIGS. 5(a) and (b).

Figure 4B:
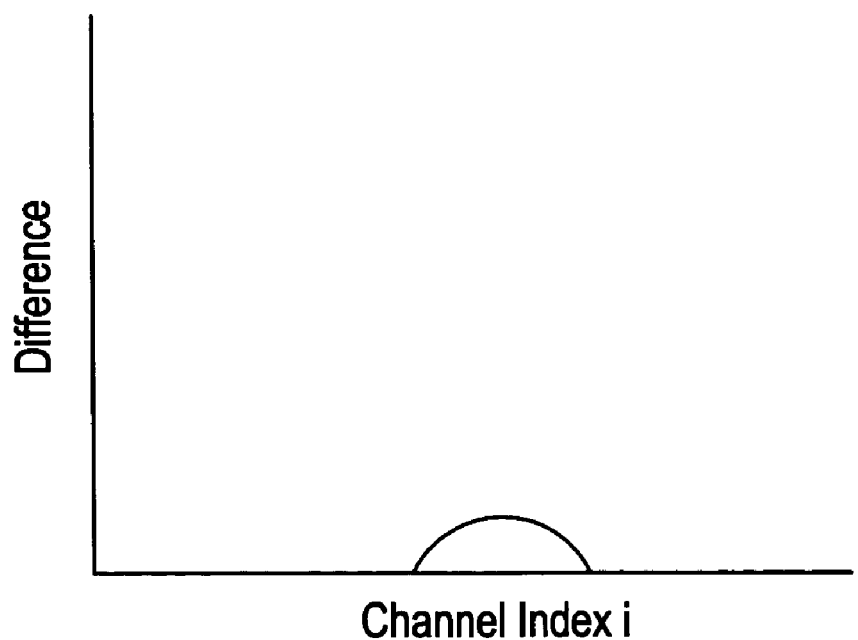
Figure 5A:
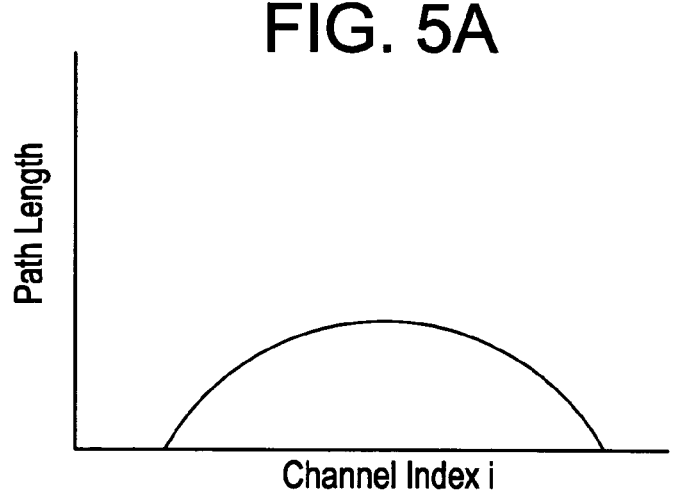
FIG. 5 is a graph representing the path length in one detector channel row, in which (a) shows exemplary values in a certain view, and (b) shows exemplary values in another view.
Figure 5B:
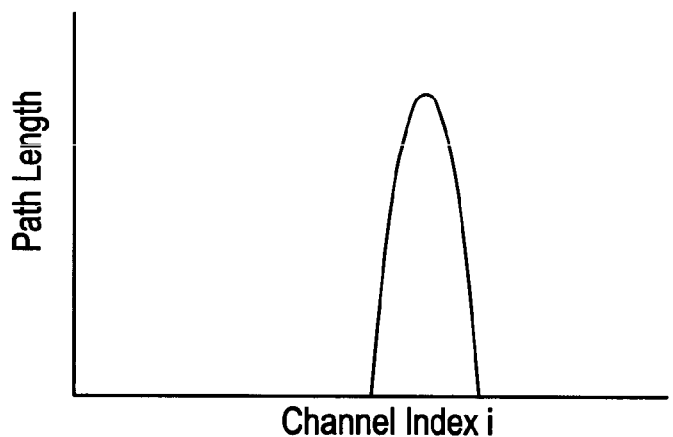

In the graphs shown in FIGS. 5(a) and (b), the horizontal axis represents the channel index i in one detector channel row 7, and the vertical axis represents the value of the data LD(m) as the path length. Moreover, FIG. 5(a) shows exemplary values in a certain view corresponding to FIG. 4(a), and FIG. 5(b) shows exemplary values in another view corresponding to FIG. 4(b).

The calculation/control apparatus 23 stores the generated data LD(m) in the storage device 40.

The calculation/control apparatus 23 accesses the storage device 40 to read the ratio Sub(m)/RD(m) and data LD(m) stored therein, and plots the ratio Sub(m)/RD(m) against the data LD(m) (Step ST10).

Figure 6:
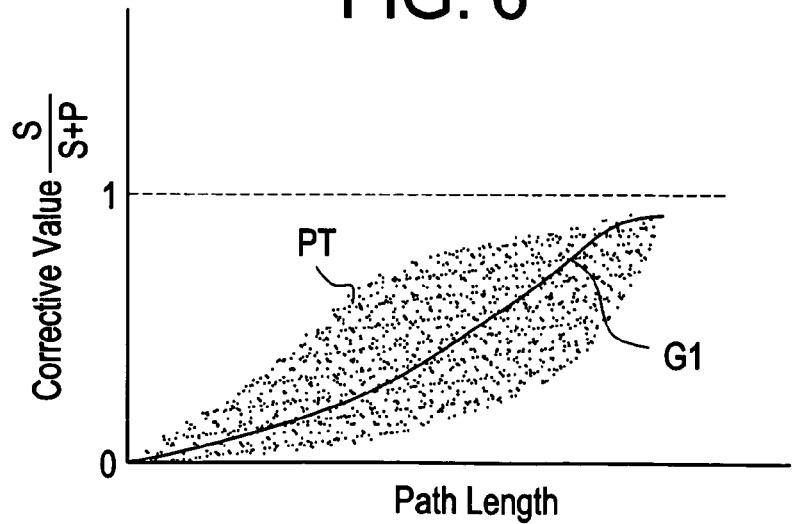
FIG. 6 is a graph representing the relationship between the path length and corrective value obtained by the calibration procedure shown in FIG. 2.

This process provides a plot PT as shown in FIG. 6. In the graph of FIG. 6, the horizontal axis represents the value of the data LD(m) as the path length, and the vertical axis represents the value of the ratio Sub(m)/RD(m) as the corrective value S/(S+P). Since the corrective value S/(S+P) is the proportion of the intensity S of scatter rays in the value of the intensity (S+P) detected by each detector channel ch, its maximum value is one.

It should be noted that the graph of FIG. 6 need not be actually generated, and the calculation/control apparatus 23 makes correspondence between the path length and corrective value as if the graph of FIG. 6 were being depicted.

Once the aforementioned procedure has been executed, the calculation/control apparatus 23 makes decision as to whether the value m of the counter has reached the number of counts n specified at Step ST1 (Step ST11).

If the number of counts n has not been reached, the calculation/control apparatus 23 increments the value m of the counter by one to redefine it as m+1 (Step ST12), and repeats the procedure from Step ST4 to Step ST10.

FIG. 7 is a perspective view of a main portion representing the relationship among the X-ray source XL, X-ray focal spot 3, X-ray beam 5 and X-ray detector 70.

In the loop of Steps ST4-ST10, the width of opening AP(m) at Step ST4 is changed so that the width of the X-ray beam 5 varies at least in the column direction (z-axis direction) in the X-ray detector 70, as shown in FIG. 7. This is because, as described earlier, the detecting surface Su of each detector channel ch forms a curve to be directed toward the X-ray focal spot 3 in the channel direction represented by the index i, and the detecting surface Su is flatly arranged in the column direction represented by the index j.

When the detecting surface Su is arranged not always to be directed toward the X-ray focal spot 3 forming a curve, as in the column direction, the width of opening AP is adjusted to enlarge the width of the X-ray beam 5 from, for example, a width L1 to a width L2, whereby the influence by scatter rays is made larger accordingly. Thus, to study the intensity of scatter rays, the width of the X-ray beam 5 is preferably adjusted in the column direction.

After Steps ST4-ST11 have been repeated to reach m=n, the calculation/control apparatus 23 goes to the next step.

If a circular cylindrical phantom is employed instead of the elliptical phantom PM at Step ST3, a decision is made here as to whether another circular cylindrical phantom having a different diameter is to be used instead (Step ST13).

When a circular cylindrical phantom is employed, the procedure goes back to Step ST2 to change the value m of the counter representing the number of times of change of parameters back to m=0, and at Step ST3, another circular cylindrical phantom having a different diameter is substituted.

Thereafter, the process from Step ST4 to ST12 is repeated.

When the process of Step ST2-ST12 has been completed for all of a plurality of circular cylindrical phantoms having different diameters to be processed, the decision that the phantom will not be replaced is made at Step ST13, and the procedure goes to the next step.

The circular cylindrical phantoms to be employed are those having a plurality of sizes, such as cross-sectional diameters of 20 cm, 30 cm, 40 cm and the like, for example.

When the process up to Step ST13 has been completed and the plot PT representing the relationship between the path length and corrective value for each detector channel ch has been obtained for all views, the calculation/control apparatus 23 executes fitting to regress the plot PT to a certain function (Step ST14).

The calculation/control apparatus 23 regresses the corrective value to a function of a certain number of orders by, for example, a method of least squares for minimizing the sum of the differences with respect to the plot PT. An exemplary graph obtained by the fitting is shown in FIG. 6 as a fitting curve graph G1.

As shown by the graph G1, the function to which the plot PT is regressed is preferably one that has a value of zero at a path length of zero.

The calibration scan has now been completed, and the corrective value normalized to the path length can be obtained in a functional form as shown by the graph G1 in FIG. 6.

The corrective value obtained from the graph G1 has a value correlated with the path length, as can be seen from the graph G1 being a function of the path length. The relationship between the path length and corrective value as shown by the graph G1 is stored in the storage device 40 as a correction table.

Figure 8:
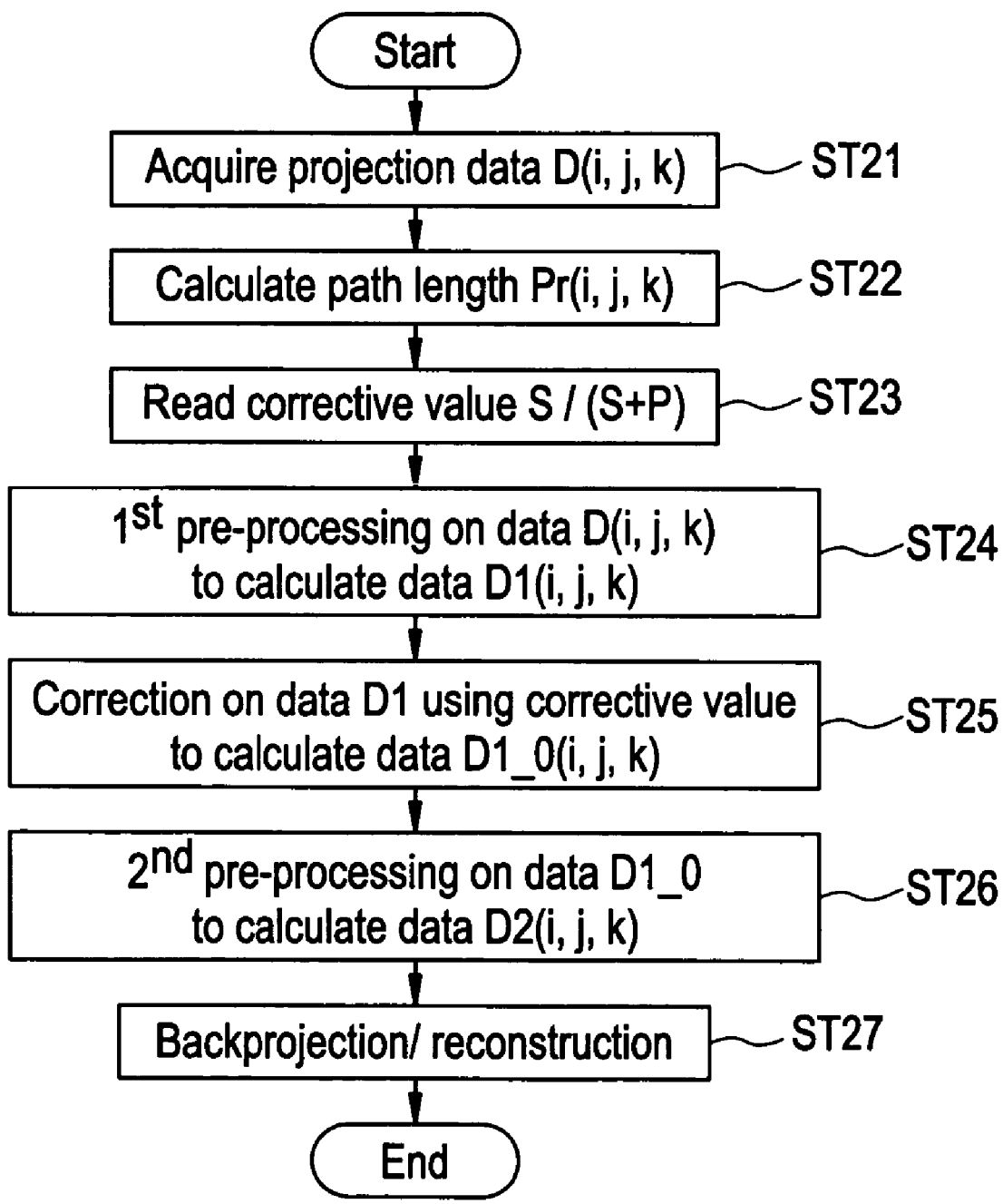
FIG. 8 is a chart showing a procedure for generating tomographic image data using the corrective value in accordance with one embodiment of the present invention.

Now a procedure for generating tomographic image data of the subject 1 using the corrective value obtained in the calibration scan will be described with reference to FIG. 8. FIG. 8 is a chart showing a procedure of generating tomographic image data using the corrective value in the present embodiment.

The calculation/control apparatus 23 first conducts a scan on the subject 1 by controlling the X-ray CT apparatus main body 10A. The scan provides projection data D(i, j, k) on the subject 1 for a channel index i, column index j, and view index k (Step ST21).

The scan has been described earlier and explanation thereof will be omitted.

The calculation/control apparatus 23 calculates a path length Pr(i, j, k) of the X-ray beam 5 detected by each detector channel ch through the subject 1 for the channel index i, column index j and view index k, based on the projection data D(i, j, k) (Step ST22).

As has been described for the calibration procedure shown in FIG. 2, a value obtained by applying first and second pre-processing on the projection data D(i, j, k) can be regarded as the path length Pr(i, j, k).

The calculation/control apparatus 23 reads a corrective value based on the path length Pr(i, j, k) calculated at Step ST22 (Step ST23).

The calculation/control apparatus 23 accesses the storage device 23 to read a corrective value corresponding to the value of the path length Pr(i, j, k) from the correction table. The calculation/control apparatus 23 uses a value after applying the second pre-processing to the corrective value obtained from the correction table based on the fitting curve as shown by the graph G1 as the corrective value S/(S+P) for correction hereinbelow.

The second pre-processing for calculating the corrective value S/(S+P) is the same as the second pre-processing such as negative logarithm at Step ST9 in FIG. 2.

The corrective value S/(S+P) corresponding to the path length Pr(i, j, k) can now be obtained for the projection data D(i, j, k).

Hereafter, tomographic image data for the subject 1 will be generated by correcting the projection data D(i, j, k) using the corrective value S/(S+P).

In generating tomographic image data, the calculation/control apparatus 23 applies first pre-processing to the projection data D(i, j, k) (Step ST24).

The first pre-processing at Step ST24 is the same as the first pre-processing such as offset and reference corrections at Step ST6 in FIG. 2.

The data obtained after applying the first pre-processing calculation to the projection data D(i, j, k) is designated as data D1 (i, j, k).

The calculation/control apparatus 23 corrects the data D1 (i, j, k) using the corrective value obtained at Step ST23 (Step ST25).

Specifically, for example, the data D1 (i, j, k) is multiplied by 1-S/(S+P) to calculate corrected data D1_0 (i, j, k).

The calculation/control apparatus 23 applies second pre-processing to the calculated data D1_0 (i, j, k), for reconstructing tomographic image data (Step ST26).

The second pre-processing is the same as that at Step ST9 in FIG. 2.

The data D1_0 (i, j, k) after the second pre-processing is designated as data D2 (i, j, k).

The calculation/control apparatus 23 performs arithmetic processing of backprojection and image reconstruction on the data D2 (i, j, k) to generate image data of a certain cross section of the subject 1, i.e., tomographic image data (Step ST27).

The tomographic image data generated may be stored in the storage device 40, or displayed on the display device 25 after post-processing including prespecified image processing such as rendering.

As described above, in the present embodiment, a corrective value S/(S+P) for correcting the influence by scatter rays can be precisely obtained by correlating the value with the path length Pr of the X-ray beam 5 through the subject 1 by a calibration scan.

Since the corrective value S/(S+P) is generated while taking various parameters such as the width of opening AP of the X-ray beam into account in the calibration scan, the value incorporates various conditions in agreement with the actual scan on the subject 1. Moreover, a portion in which the path length is zero, i.e., the subject 1 is not present, as shown in the graph G1 of the fitting curve in FIG. 6, has a corrective value S/(S+P) of zero, and no correction is made. Thus, by using the corrective value S/(S+P) in accordance with the present embodiment, a tomographic image subjected to a suitable correction in agreement with the actual scan on the subject 1 can be obtained with high image quality. Since the influence by scatter rays is effectively corrected, the present embodiment is effective especially when the X-ray detector 70 has more rows and the influence by scatter rays is larger.

Moreover, when the corrective value S/(S+P) as in the present embodiment is used to reduce the influence by scatter rays, hardware for the X-ray CT apparatus 10 needs no special modification, and correction on the influence by scatter ray can be easily practiced.

(Variation)

The procedure for generating tomographic image data using the corrective value S/(S+P) is not limited to that shown in FIG. 8, and may be implemented by other procedures. Another procedure for generating tomographic image data using the corrective value S/(S+P) will now be described with reference to FIG. 9.

FIG. 9 is a chart showing another procedure for generating tomographic image data using the corrective value S/(S+P).

The procedure through Steps ST21-ST24 shown in FIG. 9 is the same as that in FIG. 8, and detailed description thereof will be omitted.

In the variation shown in FIG. 9, instead of making correction on the data D1 (i, j, k) using the corrective value S/(S+P), the correction is made on the data D1 (i, j, k) after the second pre-processing using the corrective value S/(S+P) (Step ST30).

Specifically, for example, the calculation/control apparatus 23 applies pre-processing similar to the second pre-processing at Step ST26 in FIG. 8 to the data D1 (i, j, k) to calculate data D1_1 (i, j, k). The data D1_1 (i, j, k) is then multiplied by 1-S/(S+P) to correct the data D1_1 (i, j, k), and calculate the data D2 (i, j, k).

The calculation/control apparatus 23 executes a procedure of backprojection and reconstruction similar to Step ST27 in FIG. 8 using the calculated data D2 (i, j, k) to generate tomographic image data of a certain cross-sectional plane of the subject 1.

As described above, according to the present variation, tomographic image data for the subject 1 can be generated also by the procedure as shown in FIG. 9.

While the procedure shown in FIG. 8 and that shown in FIG. 9 are different in time of the correction using the corrective value S/(S+P), they are ultimately procedures in which mathematically equivalent processing is applied. Therefore, a tomographic image obtained by the procedure shown in FIG. 9 is the same as that obtained by the procedure shown in FIG. 8, and a similar effect of improvement of image quality can be obtained.

It should be noted that the present invention is not limited to the aforementioned embodiment and its variation, and several modifications may be done. For example, the procedure of the calibration scan is not limited to that shown in the flow chart of FIG. 2, and any procedure that provides the same effect can be adopted. Moreover, the corrective value S/(S+P) may incorporate not only the width of opening AP but other parameters including a region in the tomographic image to be reconstructed or the voltage applied to the X-ray source XL.

Furthermore, to acquire the projection data, not only x-rays but also other radiation such as gamma rays may be employed. In addition, by using a cylindrical X-ray detector instead of the rotating section 2, a radiation computed tomography apparatus having a configuration for acquiring projection data without using a rotation mechanism may be employed.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation computed tomography apparatus comprising:
   a radiation source;
   a radiation detector having a plurality of radiation detector elements arranged in a two-dimensional manner which is placed opposite to said radiation source so as to detect radiation exposed from said radiation source and passing through a subject positioned between said radiation source and said radiation detector; and
   a reconstructing device for reconstructing a tomographic image of said subject based on projection data for said subject from each of said plurality of radiation detector elements, said projection data obtained from values detected by said plurality of radiation detector elements, wherein said reconstructing device includes a correcting device configured to correct said projection data for each of said radiation detector elements by using a corrective value to reduce projection information by an effect of a plurality of scatter rays which should not be detected, wherein the corrective value is correlated with a path length of said radiation through said subject and with a width of an opening of a collimator configured to restrict the radiation.

2. The radiation computed tomography apparatus of claim 1, wherein:

said corrective value is a value obtained based on a calibration scan by using a phantom differentiating said path length as said subject.

3. The radiation computed tomography apparatus of claim 2, wherein:

said radiation detector rotates around said phantom about a pre-determined axis of rotation;

said plurality of radiation detector elements extend in a two-dimensional manner in two arrangement directions, one being a first arrangement direction, the other being a second arrangement direction orthogonal to said first arrangement direction; and said plurality of radiation detector elements are arranged to form a curve along the direction of rotation around said axis of rotation in said first arrangement direction, and are flatly arranged in said second arrangement direction.

4. The radiation computed tomography apparatus of claim 2, wherein:

a plurality of sets of said projection data having different path lengths are acquired by detecting said radiation passing through said phantom having an elliptical cross section in a plurality of directions around said phantom by said radiation detector, said projection data is subjected to at least one computation to obtain values as additional data, and said additional data is subjected to fitting to a certain function with respect to said path length to obtain a value as said corrective value.

5. The radiation computed tomography apparatus of claim 4, wherein:

a difference between said projection data acquired at a reference width of opening of the collimator and said projection data acquired at a width of opening of the collimator different from said reference width of opening is used as said additional data for said corrective value.

6. The radiation computed tomography apparatus of claim 5, wherein:

said additional data is calculated based on said projection data acquired at a plurality of said widths of opening of the collimator different from said reference width of opening.

7. The radiation computed tomography apparatus of claim 3, wherein:

said width of opening is changed in said second arrangement direction of said plurality of radiation detector elements.

8. A tomographic image data generating method in a radiation computed tomography apparatus comprising a radiation detector having a plurality of radiation detector elements arranged in a two-dimensional manner for detecting radiation passing through a subject, and a reconstructing device for reconstructing tomographic image data of said subject based on projection data for said subject from each of said plurality of radiation detector elements, said method comprising:

correcting said projection data obtained from each of the radiation detectors elements by using a corrective value to reduce projection information by an effect of a plurality of scatter rays which should not be detected, wherein the corrective value is correlated with a path length of radiation through a subject and with a width of an opening of a collimator configured to restrict the radiation; and generating said tomographic image data based on said projection data.

9. The tomographic image data generating method of claim 8, wherein:

said corrective value is a value obtained based on a calibration scan conducted by using a phantom differentiating said path length as said subject.

10. The tomographic image data generating method of claim 9, wherein:

said radiation detector is rotated around said phantom about a pre-determined axis of rotation; and projection data obtained by emitting a beam of said radiation onto said plurality of radiation detector elements is employed as said projection data, said plurality of radiation detector elements arranged in a two-dimensional manner in two arrangement directions, one being a first arrangement direction, the other being a second arrangement direction orthogonal to said first arrangement direction, said plurality of radiation detector elements arranged to form a curve along the direction of rotation around said axis of rotation in said first arrangement direction, and flatly arranged in said second arrangement direction, said beam of said radiation extending said two arrangement directions.

11. The tomographic image data generating method of claim 9, wherein:

a plurality of sets of said projection data having different path lengths are acquired by detecting said radiation passing through said phantom having an elliptical cross section in a plurality of directions around said phantom by said radiation detector, said projection data is subjected to at least one computation to obtain values as additional data, and said additional data is subjected to fitting to a certain function with respect to said path length to obtain a value as said corrective value.

12. The tomographic image data generating method of claim 11, wherein:

a difference between said projection data acquired at a reference width of opening of the collimator and said projection data acquired at a width of opening different from said reference width of opening is used as said additional data for said corrective value.

13. The tomographic image data generating method of claim 12, wherein:

said additional data is calculated based on said projection data acquired at a plurality of said widths of opening of the collimator different from said reference width of opening.

14. The tomographic image data generating method of claim 10, wherein:

said width of opening is changed in said second arrangement direction of said plurality of radiation detector elements.

15. The radiation computed tomography apparatus of claim 1, wherein the corrective value is based on an intensity of the scatter rays.

16. The radiation computed tomography apparatus of claim 1, wherein the corrective value is based on a ratio of an intensity of scatter rays to an intensity of all rays detected by each channel.

17. The radiation computed tomography apparatus of claim 1 wherein the corrective value is based on a proportion of intensities of said plurality of scatter rays.

18. The radiation computed tomography apparatus of claim 1, wherein said radiation detector is further configured to acquire at least said projection data and data from said plurality of scatter rays.

* * * * *